(12) United States Patent
Dwork

(10) Patent No.: US 8,790,386 B2
(45) Date of Patent: Jul. 29, 2014

(54) CATHETER HANDLE AND METHODS OF OPERATING

(75) Inventor: Joshua Dwork, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 350 days.

(21) Appl. No.: 13/106,110

(22) Filed: May 12, 2011

(65) Prior Publication Data

US 2011/0282425 A1 Nov. 17, 2011

Related U.S. Application Data

(60) Provisional application No. 61/334,839, filed on May 14, 2010.

(51) Int. Cl.
*A61F 2/06* (2013.01)

(52) U.S. Cl.
USPC .............................................. 623/1.11; 606/1

(58) Field of Classification Search
USPC ............ 606/1, 107, 108, 109; 623/1.11, 1.12, 623/1.23, 6.12
See application file for complete search history.

(56) References Cited

U.S. PATENT DOCUMENTS 7,419,501 B2 9/2008 Chiu et al.

FOREIGN PATENT DOCUMENTS

| EP | 1302178 | 4/2003 |
|----|---------|--------|
| EP | 1806114 | 7/2007 |
| WO | WO2005/067819 | 7/2005 |
| WO | WO2005/070095 | 8/2005 |

*Primary Examiner* — Jonathan W Miles

(57) ABSTRACT

A delivery system having an improved handle allowing operation of the delivery system with one hand while maintaining accuracy in delivery and deployment of a prosthesis in a body lumen. The delivery system includes a sheath and a handle. The handle includes a slide shaft having a threaded outer surface, and a hub assembly coupled to the sheath. The hub assembly includes an inner slider having a thread tooth pivot support, a thread tooth pivotally mounted to the thread tooth pivot support, a distal sleeve having a thread tooth press member pressing on the thread tooth, and a proximal sleeve. Motion of the distal sleeve relative to the inner slider pivots the thread tooth on the thread tooth pivot support to engage and disengage the hub assembly with the threaded outer surface. The distal sleeve is rotatably coupled to the proximal sleeve, and the proximal sleeve is prevented from rotating to provide a stable grip to allow operation of the catheter with one hand.

12 Claims, 10 Drawing Sheets

CATHETER HANDLE AND METHODS OF OPERATING

CROSS-REFERENCE TO RELATED APPLICATION

This application claims the benefit of U.S. Provisional Application No. 61/334,839, filed May 14, 2010, the entire disclosure of which is incorporated by reference in its entirety herein.

BACKGROUND OF THE INVENTION

1. Field of the Invention

The present invention relates to devices and methods for delivering a prosthesis to a desired location in the body and methods for achieving delivery and implantation of a prosthesis. More particularly, the present invention relates to a delivery system for deploying prostheses within a body lumen and to methods of delivering prostheses to a desired location in a body. The delivery system includes a handle that can be operated with one hand while maintaining accuracy in deployment of a prosthesis in a body lumen.

2. Background

Vascular aneurysms are the result of abnormal dilation of a blood vessel, usually resulting from disease and/or genetic predisposition, which weakened the arterial wall and allowed it to expand. While aneurysms could occur in any blood vessel, most occur in the aorta and peripheral arteries, with the majority of aortic aneurysms occurring in the abdominal aorta, usually beginning below the renal arteries and often extending into one or both of the iliac arteries.

Aortic aneurysms were commonly treated in open surgical procedures where the diseased vessel segment was bypassed and repaired with an artificial vascular graft. While considered to be an effective surgical technique, particularly considering the alternative of a fatal ruptured abdominal aortic aneurysm, conventional vascular graft surgery suffered from a number of disadvantages. The surgical procedure was complex and required experienced surgeons and well-equipped surgical facilities. Even with the best surgeons and equipment, however, patients being treated frequently were elderly and weakened from cardiovascular and other diseases, reducing the number of eligible patients.

Even for eligible patients prior to rupture, conventional aneurysm repair had a relatively high mortality rate, usually from 2% to 10%. Morbidity related to the conventional surgery included myocardial infarction, renal failure, impotence, paralysis, and other conditions. Additionally, even with successful surgery, recovery took several weeks, and often required a lengthy hospital stay.

In order to overcome some or all of these drawbacks, endovascular prosthesis placement for the treatment of aneurysms has been used. Although very promising, many of the proposed methods and apparatus suffered from undesirable limitations. In particular, accurate delivery and placement of the endovascular prosthesis within the vasculature was problematic.

Stent-grafts (endovascular prostheses) were resilient structures, usually biased to expand against the surrounding lumenal wall. Such resiliently-expanding stent-grafts were tightly compressed within the catheter, imposing significant radial expansion forces against the surrounding catheter sheath. This often led to excess friction between the stent-graft and the sheath, particularly when the resiliently-expanding structure becomes partially embedded in the catheter material. Thus, the delivery system had to be capable of imparting a significant, yet controlled, force to retract the sheath and deploy the stent-grafts.

U.S. Pat. No. 7,419,501 to Chiu et al., which is incorporated herein by reference in its entirety, discloses a delivery system that attempts to address these issues by providing a delivery system having a handle that allows for more accurate placement of a stent-graft in a body lumen. The delivery system includes a sheath and a handle. The handle includes a slide shaft having a threaded outer surface, and a hub assembly coupled to the sheath. The hub assembly includes an inner slider having a thread tooth pivot support, a thread tooth pivotably mounted to the thread tooth pivot support, and a sleeve having a thread tooth press member pressing on the thread tooth, where motion of the sleeve relative to the inner slider pivots the thread tooth on the thread tooth pivot support to engage and disengage the hub assembly with the threaded outer surface. FIGS. 1-2 and 4-7 of the present application have been adapted from figures originally presented in U.S. Pat. No. 7,419,501.

BRIEF SUMMARY OF THE INVENTION

The present invention provides a delivery system having an improved handle that allows for operation of the delivery system with one hand while maintaining accuracy in delivery and deployment of a prosthesis in a body lumen. The delivery system includes a sheath and a handle. The handle includes a slide shaft having a threaded outer surface, and a hub assembly coupled to the sheath. The hub assembly includes an inner slider having a thread tooth pivot support, a thread tooth pivotably mounted to the thread tooth pivot support, a distal sleeve having a thread tooth press member pressing on the thread tooth, and a proximal sleeve. Motion of the distal sleeve relative to the inner slider pivots the thread tooth on the thread tooth pivot support to engage and disengage the hub assembly with the threaded outer surface. The distal sleeve is rotatably coupled to the proximal sleeve, and the proximal sleeve is prevented from rotating to provide a stable grip to allow operation of the catheter with one hand.

BRIEF DESCRIPTION OF THE FIGURES

The accompanying figures, which are incorporated herein, form part of the specification and illustrate embodiments of catheter delivery systems and methods of delivering prostheses to a desired location in a body. Together with the description, the figures further serve to explain the principles of and to enable a person skilled in the relevant art(s) to make and use the delivery systems and methods described herein. In the drawings, like reference numbers indicate identical or functionally similar elements.

FIG. 1 is a modification of FIG. 14 of U.S. Pat. No. 7,419,501.

FIG. 2 is a modification of FIG. 16 of U.S. Pat. No. 7,419,501.

FIG. 4 is a modification of FIG. 17 of U.S. Pat. No. 7,419,501.

FIG. 5 is a modification of FIG. 20 of U.S. Pat. No. 7,419,501.

FIG. 6 is a modification of FIG. 21 of U.S. Pat. No. 7,419,501.

FIG. 7 is a modification of FIG. 22 of U.S. Pat. No. 7,419,501.

DETAILED DESCRIPTION OF THE INVENTION

The following detailed description of catheter delivery systems and methods of delivering prostheses to a desired location in a body refers to the accompanying figures that illustrate exemplary embodiments. Other embodiments are possible. Modifications can be made to the embodiments described herein without departing from the spirit and scope of the present invention. Therefore, the following detailed description is not meant to be limiting. Further, it would be apparent to one of skill in the art that the systems and methods described below can be implemented in many different embodiments of hardware. Any actual hardware described is not meant to be limiting. The operation and behavior of the systems and methods presented are described with the understanding that modifications and variations of the embodiments are possible given the level of detail presented.

Figure 1:
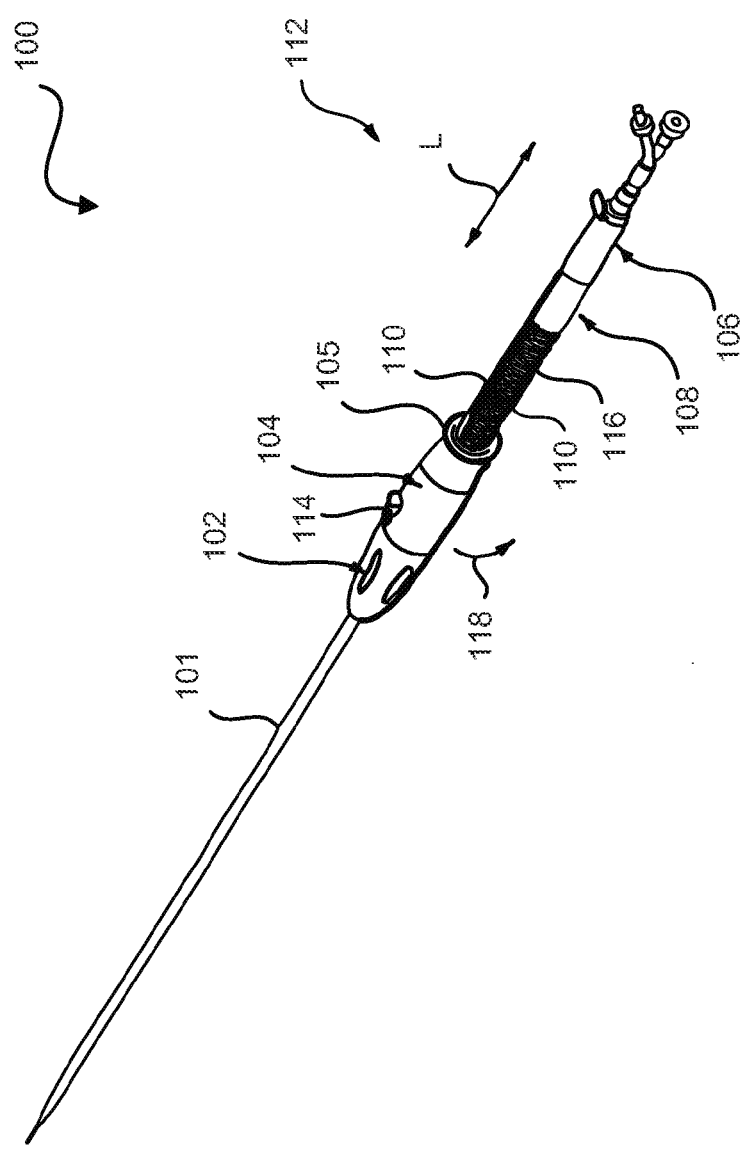
FIG. 1 illustrates a delivery system in accordance with one embodiment presented herein.

FIG. 1 depicts a perspective view of a delivery system 100 according to one embodiment of the present invention. Delivery system 100 includes a handle assembly 112. Handle assembly 112 includes a distal housing 102, sometimes called a front grip, a hub assembly 104, sometimes called a rotating external slider, a sliding grip 105, and a proximal housing 106, sometimes called a rear grip. Handle assembly 112 further includes a slide shaft 108, sometimes called a screw gear, extending between distal housing 102 and proximal housing 106. Slide shaft 108 is a hollow tubular member and includes opposing slots 110. In one embodiment, slots 110 extend through the entire thickness of slide shaft 108. In other embodiment, slots 100 extend through a partial thickness of slide shaft 108. Slide shaft 108 includes a threaded outer surface 116, e.g., a buttress thread.

Hub assembly 104 is selectively engaged and disengaged with threaded outer surface 116 of slide shaft 108 by motion of a thumb slider 114, sometimes called an actuation button. Sliding grip 105 does not engage threaded outer surface 116. Sliding grip 105 includes inwardly extending tabs 1001 (see FIG. 10) that extend through slots 110 to secure sliding grip 105 to slide shaft 108. In this configuration, sliding grip 105 can slide proximally and distally along slide shaft 108, but rotation of sliding grip 105 is prevented. Hub assembly 104 can be connected to sliding grip 105 such that hub assembly 104 can rotate relative to sliding grip 105. The operation and structure of sliding grip 105 with respect to hub assembly 104 is described in further detail with reference to FIGS. 8-10.

Figure 2:
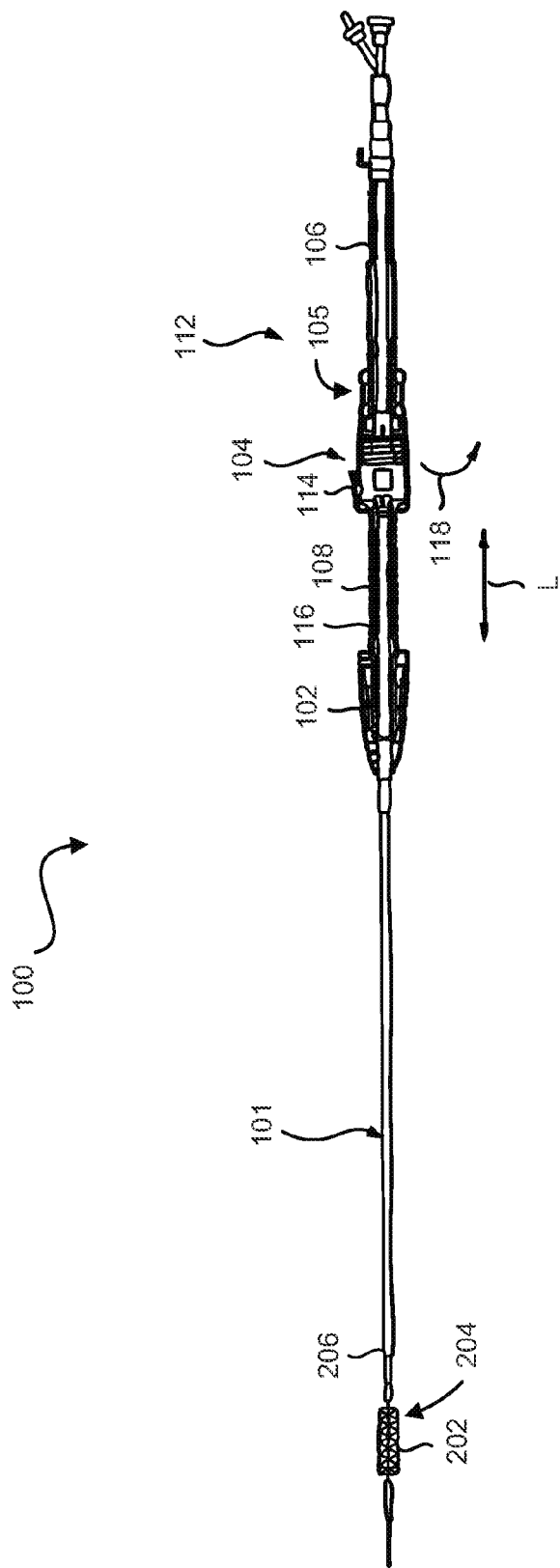
FIG. 2 a side view, partially in cross-section, of the delivery system of FIG. 1 after retraction of a sheath.

When engaged, i.e., threadedly attached, with threaded outer surface 116 of slide shaft 108, axial rotation of hub assembly 104 as indicated by arrow 118 is converted into axial translation, i.e., retraction, of sheath 101 of delivery system 100. As sheath 101 is refracted, a prosthesis 202, which is mounted within sheath 101, can be held in position by a prosthesis retainer (not shown) mounted on a delivery shaft (not shown). As shown in FIG. 2, as sheath 101 is retracted, prosthesis 202 exits the distal end 206 of sheath 101. Sheath 101 is coupled to hub assembly 104. As a result, proximal end 204 of prosthesis 202 is gradually released through axial rotation of hub assembly 104. In this manner, the physician can verify the accuracy of the deployment position as prosthesis 202 initially engages the surrounding body lumen.

Non-rotating sliding grip 105 allows for a physician to operate delivery system 100 with one hand. The pad of a user's hand can grip the sliding grip 105 while the user rotates hub assembly 104 with his or her fingers to control axial movement of sheath 106.

Further, when pressure is applied to thumb slider 114 and the hub assembly 104 is thereby disengaged from threaded outer surface 116 of slide shaft 108, hub assembly 104 is slidably mounted on slide shaft 108. Thus, when pressure is applied to thumb slider 114, hub assembly 104 can be easily and quickly slid along slide shaft 108. No rotation of hub assembly 104 is required to return the hub assembly 104 to its initial position when the hub assembly 104 is disengaged from threaded outer surface 116. By sliding hub assembly 104, sheath 101 is easily and quickly retracted, thus rapidly completing deployment of prosthesis 202. Rapid deployment of prosthesis 202 facilitates faster procedure times, thus minimizing the period of time during which blood flow is occluded.

In one embodiment, as described above, sheath 101 can be retracted by the combination of axial rotation of hub assembly 104 followed by sliding, i.e., axial translation, of hub assembly 104 along a longitudinal axis L of handle 112. In another embodiment, sheath 101 is refracted entirely by axial rotation of hub assembly 104. Further, in yet another embodiment, sheath 101 is retracted entirely by sliding of hub assembly 104 along longitudinal axis L of handle 112.

In one embodiment, hub assembly 104 is initially engaged with threaded outer surface 116 of slide shaft 108. Sheath 101 is initially retracted by axial rotation of hub assembly 104. Hub assembly 104 is then disengaged from threaded outer surface 116 of slide shaft 108. Sheath 101 is further retracted by sliding of hub assembly 104 along longitudinal axis L of handle assembly 112. Hub assembly 104 is again engaged with threaded outer surface 116 of slide shaft 108, for example, if the deployment force, e.g., friction, increases and the physician desires more mechanical advantage for further deployment of sheath 101. Sheath 101 is then further retracted by axial rotation of hub assembly 104. In the above manner, sheath 101 is retracted rapidly by sliding hub assembly 104. However, at any time during retraction, hub assembly 104 can be engaged with threaded outer surface 116 of slide shaft 108 for more mechanical advantage and control of sheath 101.

Figure 3:
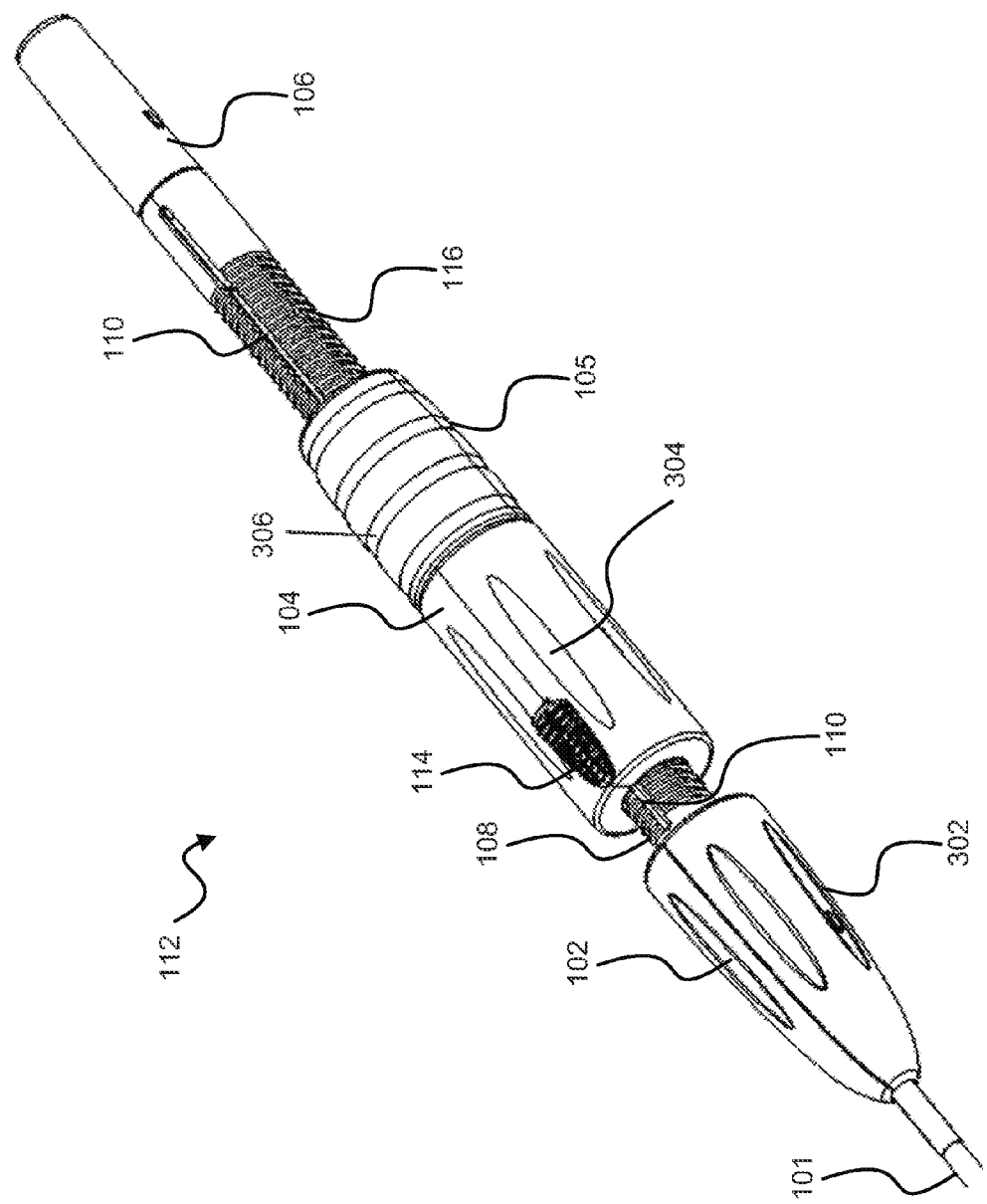
FIG. 3 is a perspective view of a handle of a delivery system according to one embodiment of the present invention.

FIG. 3 is an enlarged perspective view of handle assembly 112. As seen in FIG. 3, various types of gripping enhancements can be provided on the components of handle assembly 112. Distal housing 102 can have a plurality of longitudinally disposed grooves 302 to facilitate gripping of the distal housing 102. Alternately, ridges or a textured material can be provided on distal housing 102 to improve the gripping traction when operating the delivery system 100. Similarly, hub assembly 104 can be provided with grooves 304 to facilitate gripping and rotation of hub assembly 104. Ridges or textured materials can also be provided on hub assembly 104. Sliding grip 105 can also include grooves or ridges 306 to improve a user's grip on the handle assembly 112. Grooves or ridges 306 can be formed as circumferential rings around hub assembly 105 to provide additional grip in the axial direction. However, grooves or ridges can be formed longitudinally, as shown with respect to grooves 302 and 304, or in any other orientation that would improve a user's grip on the handle assembly 112. Grooves 302 and 304 could also be formed as circumferential rings.

Figure 4:
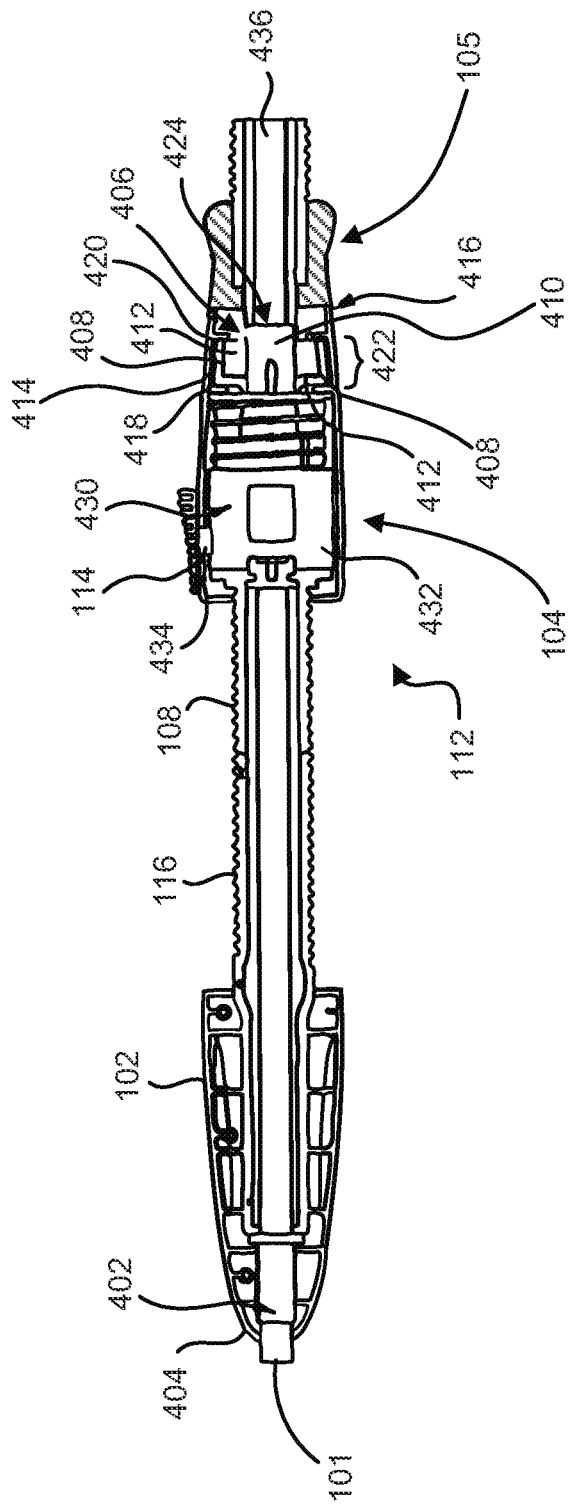
FIG. 4 is an enlarged side view, partially in cross-section, of the handle of FIG. 2.

As shown in FIG. 4, sheath 101 extends through a strain relief 402 at a distal end 404 of distal housing 102. Strain relief 402 distributes stress from distal housing 102 onto sheath 101 thus preventing kinking or other damage to sheath 101 at the location where the sheath 101 exits the front grip. Sheath 101 is coupled to a T-tube assembly 406 of hub assembly 104.

T-tube assembly 406 includes an outer body (two oppositely positioned arcuate members) 408, an inner body (tube) 410, and couplers (two oppositely, radially extending members, which can be fins) 412, which couple outer body 408 to inner body 410 as discussed further below. Each outer body 408 and coupler 412 forms the general shape of a T (see FIG. 9). In one embodiment, outer body 408 is outside of cylindrical slide shaft 108.

Outer body 408 is slidably mounted within a circumferential channel 414 of an external housing 416 of hub assembly 104. More particularly, circumferential channel 414 is defined by a distal annular stop 418, a proximal annular stop 420, and a tapering cylindrical portion 422 of external housing 416.

Distal and proximal annular stops 418 and 420 prevent longitudinal motion of outer body 408 and thus T-tube assembly 406 relative to external housing 416. However, external housing 416 is rotatable relative to outer body 408 and thus T-tube assembly 406. More particularly, as external housing 416 is rotated, outer body 408 slides with no rotation within rotating circumferential channel 414.

Inner body (tube) 410 is located within slide shaft 108. Inner body 410 includes a central aperture 424 through which a pushrod 436 extends. The proximal end of sheath 101 is attached to inner body (tube) 410, for example, using adhesive, screws, or a press fit. The distal end of inner body 410 can include one or more support rings 802 (not shown in FIG. 4) to prevent the collapse or deflection of the side walls of the slotted portion of the slide shaft 108 when engaged by the hub assembly.

As set forth above, slide shaft 108 includes opposing slots 110. Couplers 412 extend through slots 110 and couple outer body 408 of the T-tube assembly 406 to inner body 410. By extending through slots 110, couplers 412 prevent rotation of T-tube assembly 406 and thus of sheath 101 with respect to slide shaft 108.

In one embodiment, T-tube assembly 406 is integral, i.e., outer body 408, inner body 410, and couplers 412 are parts of a single piece and are not a plurality of separate pieces connected together. However, in an alternative embodiment, outer body 408, inner body 410, and/or couplers 412 are separate pieces connected together.

Hub assembly 104 further includes an internal slider subassembly 430, sometimes called a selectively engaging member. With the exception of thumb slider 114, the internal slider subassembly 430 is located within external housing 416. Thumb slider 114 is part of a sleeve 432 of internal slider subassembly 430 and extends through a thumb slider slot 434 of external housing 416. Thumb slider 114 and, thus, sleeve 432 of internal slider subassembly 430 are moved, e.g., by the physician, relative to external housing 416 to selectively engage and disengage hub assembly 104 from threaded outer surface 116 of slide shaft 108.

Figure 5:
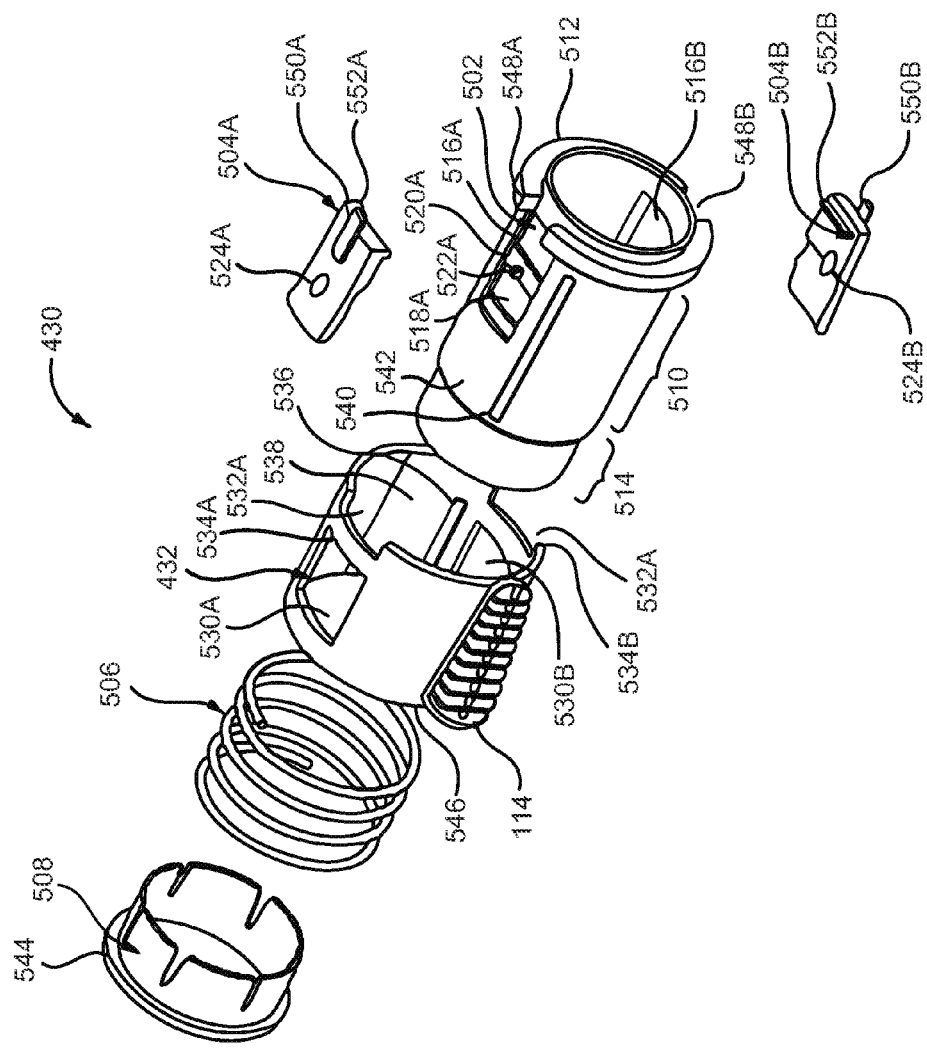
FIG. 5 is an exploded view of an internal slider subassembly according to one embodiment of the present invention.
Figure 6:
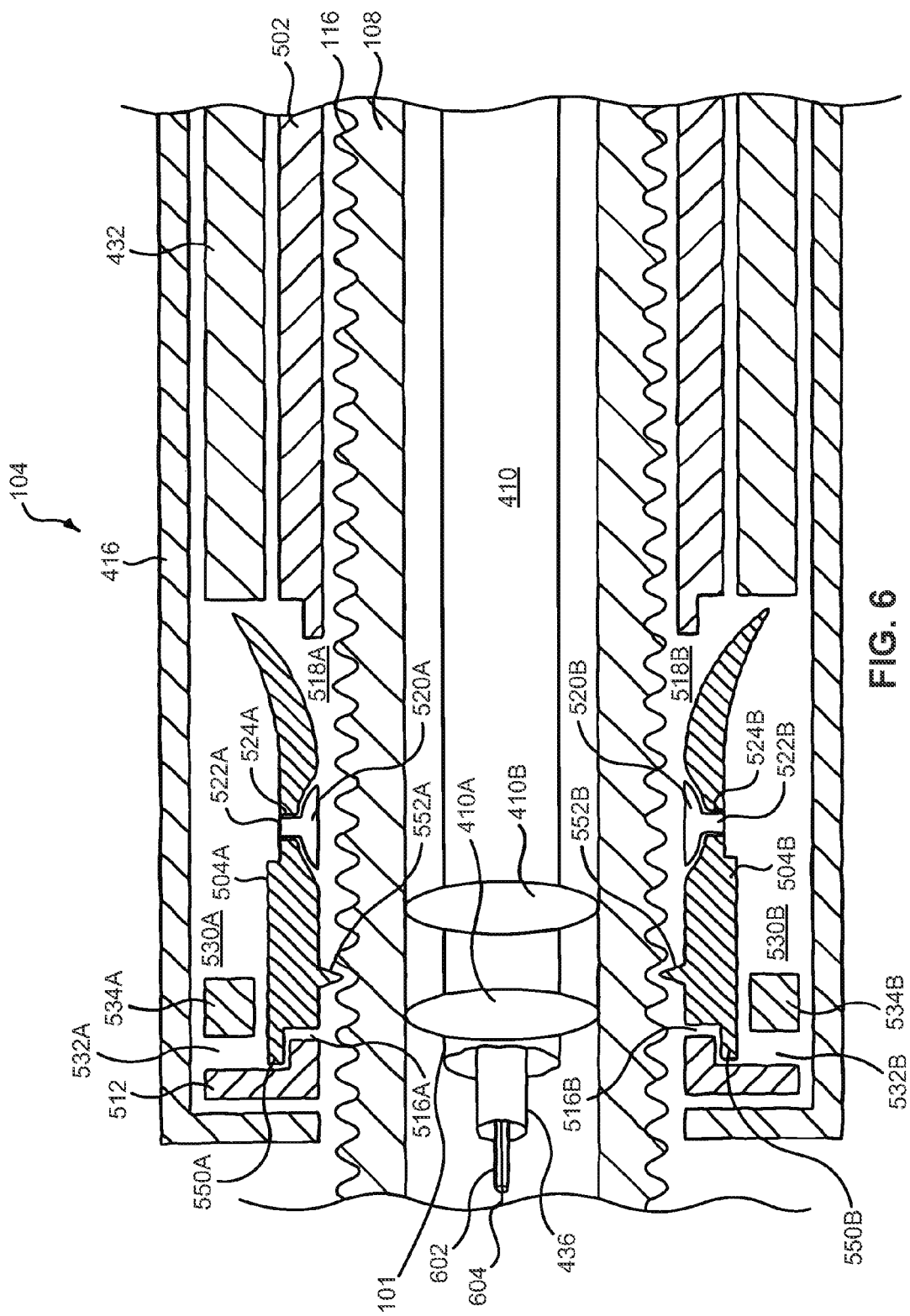
FIG. 6 is a cross-sectional and partially cutaway view of a hub assembly according to one embodiment of the present invention engaged with a threaded outer surface of a slide shaft.
Figure 7:
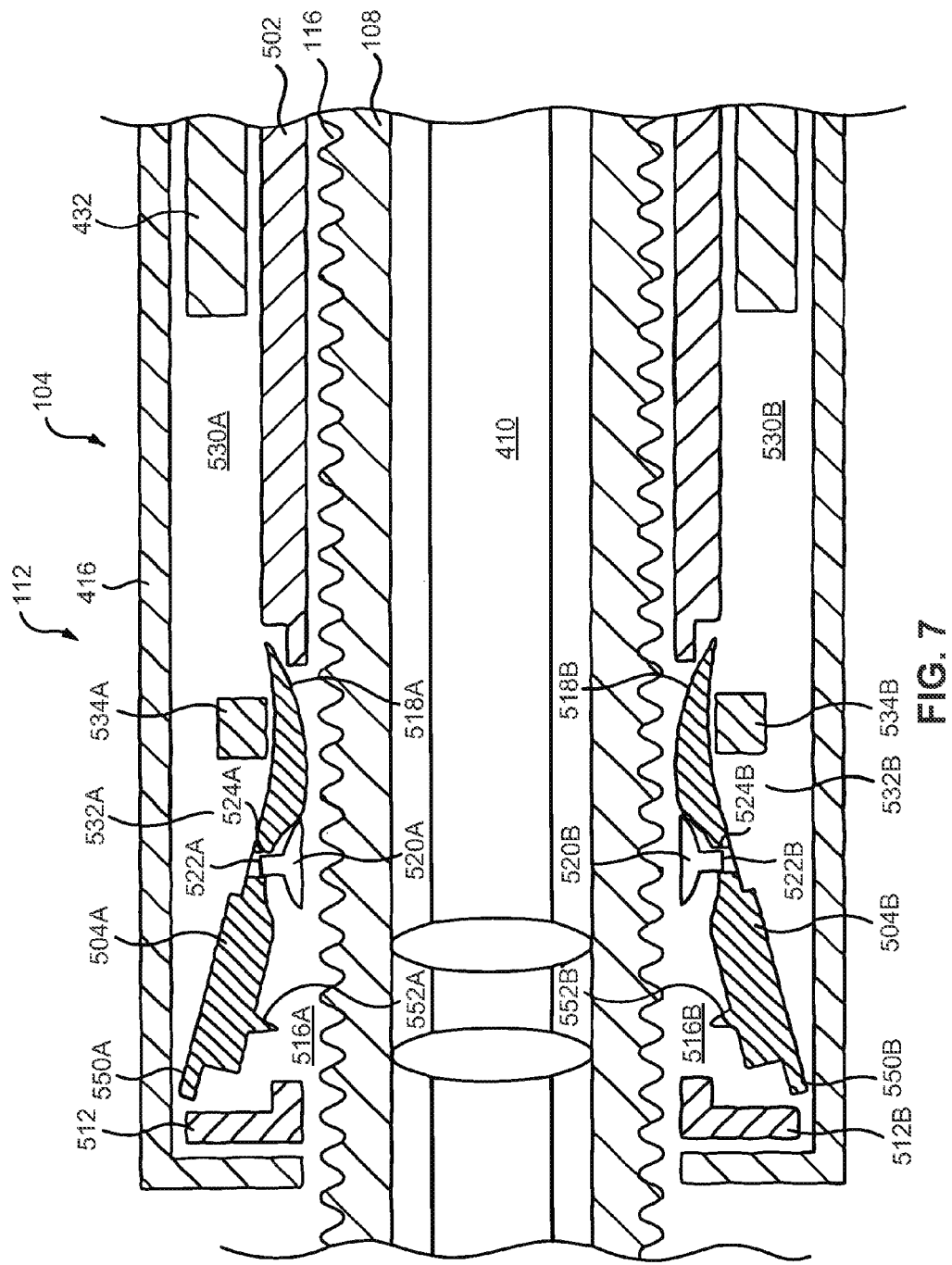
FIG. 7 is a cross sectional view of the hub assembly of FIG. 6 in a second stage of operation.

Referring now to FIGS. 5-7, internal slider subassembly 430 includes an inner slider 502, a pair of opposing thread teeth 504A, 504B, a spring 506, and a spring retainer 508. Although two thread teeth 504A, 504B are illustrated and discussed below, other numbers of thread teeth 504 and corresponding structure are used in other embodiments, e.g., one, three, four, five or more.

Inner slider 502 includes a generally cylindrical body 510, a distal stop 512, and a proximal spring retainer mounting section 514. Body 510 includes a pair of opposing distal thread teeth pivot apertures 516A, 516B, a pair of opposing proximal thread teeth pivot apertures 518A, 518B, and a pair of opposing thread teeth flat (not arc shaped) pivot supports 520A, 520B (proximal thread tooth pivot aperture 518B and thread tooth pivot support 520B are not illustrated in FIG. 5, see FIGS. 6 and 7). Collectively, distal thread teeth pivot apertures 516A, 516B, proximal thread teeth pivot apertures 518A, 518B, and thread teeth pivot supports 520A, 520B are sometimes referred to as distal or first thread teeth pivot apertures 516, proximal or second thread teeth pivot apertures 518, and thread teeth pivot supports 520, respectively.

Thread tooth pivot support 520A approximates a circumferential member, i.e., has a length along the circumference of body 510, but actually is a flat element (like the chord of a circle to the linear pivot axis). However, in another embodiment, tooth pivot support 520A is a curved circumferential member, e.g., a segment of a circle. Thread tooth pivot support 520A is between and separates distal thread tooth pivot aperture 516A and proximal thread tooth pivot aperture 518A.

Thread tooth pivot support 520A includes a protruding pivot pin 522A, which seats in a pivot pin aperture 524A of thread tooth 504A (although in one embodiment, pivot pin 522A and pivot pin aperture 524A are not used). Accordingly, thread tooth 504A is pivotally mounted to thread tooth pivot support 520A and thus inner slider 502.

As discussed further below, thread tooth 504A pivots back and forth (proximally and distally) on thread tooth pivot support 520A into and out of proximal thread tooth pivot aperture 518A and distal thread tooth pivot aperture 516A.

Thread tooth pivot support 520B is similar to thread tooth pivot support 520A. Thread tooth pivot support 520B is between and separates distal thread tooth pivot aperture 516B and proximal thread tooth pivot aperture 518B.

Thread tooth pivot support 520B includes a protruding pivot pin 522B, which seats in a pivot pin aperture 524B of thread tooth 504B (although in one embodiment, pivot pin 522B and pivot pin aperture 524B are not used). Accordingly, thread tooth 504B is pivotally mounted to thread tooth pivot support 520B and thus inner slider 502.

As discussed further below, thread tooth 504B pivots back and forth (proximally and distally) on thread tooth pivot support 520B into and out of proximal thread tooth pivot aperture 518B and distal thread tooth pivot aperture 516B.

Sleeve 432 includes a pair of opposing proximal thread teeth pivot apertures 530A, 530B, a pair of opposing distal thread teeth pivot cutouts 532A, 532B, and a pair of opposing thread teeth press members 534A, 534B. Collectively, proximal thread teeth pivot apertures 530A, 530B, distal thread teeth pivot cutouts 532A, 532B, and thread teeth press members 534A, 534B are sometimes referred to as proximal thread teeth pivot apertures 530, distal thread teeth pivot cutouts 532, and thread teeth press members 534, respectively.

Sleeve 432 is generally cylindrical and has an inner diameter slightly greater than an outer diameter of body 510 of inner slider 502. This allows sleeve 432 to be slipped over and located around body 510 of inner slider 502.

One or more longitudinal lips 536 protrude inwards from an inner surface 538 of sleeve 432. Lips 536 mate with longitudinal slots 540 in an outer surface 542 of body 510 of inner slider 502. Slots 540 have a greater length than lips 536 allowing lips 536 to be slid longitudinally back and forth within slots 540. In this manner, longitudinal motion of sleeve 432 relative to inner slider 502 is permitted while rotation of sleeve 432 relative to inner slider 502 is prevented.

Thread tooth press member 534A is a circumferential member, i.e., has a length along the circumference of sleeve 432. Thread tooth press member 534A is between and separates distal thread tooth pivot cutout 532A and proximal thread tooth pivot aperture 530A.

As discussed further below, thread tooth press member 534A presses on and pivots thread tooth 504A back and forth as sleeve 432 is moved longitudinally relative to inner slider 502.

Similarly, thread tooth press member 534B is a circumferential member, i.e., has a length along the circumference of sleeve 432. Thread tooth press member 534B is between and separates distal thread tooth pivot cutout 532B and proximal thread tooth pivot aperture 530B.

As discussed further below, thread tooth press member 534B presses on and pivots thread tooth 504B back and forth as sleeve 432 is moved longitudinally relative to inner slider 502.

Spring retainer 508 is mounted around spring retainer mounting section 514 of inner slider 502. Spring 506 is mounted around inner slider 502 and is located longitudinally between sleeve 432 and a proximal spring stop 544 of spring retainer 508.

Spring 506 is compressed between spring stop 544 of spring retainer 508 and a proximal end 546 of sleeve 432. Due to this compression of spring 506, spring 506 urges sleeve 432 distally and against distal stop 512 of inner slider 502.

Distal stop 512 of inner slider 502 includes opposing cutouts 548A, 548B, collectively cutouts 548. Thread teeth 504A, 504B include extending fingers 550A, 550B, collectively fingers 550, which seat in cutouts 548A, 548B, respectively as thread teeth 504 are pivoted. Further, thread teeth 504A, 504B include inward protruding teeth 552A, 552B, collectively referred to as protruding teeth 552.

FIG. 6 is a cross-sectional and partially cutaway view of handle assembly 112 with hub assembly 104 engaged with threaded outer surface 116 of slide shaft 108. Referring now to FIG. 6, thread teeth press members 534 are pressing on thread teeth 504 on a side opposite of protruding teeth 552. More particularly, thread teeth press members 534 press protruding teeth 552 into threaded engagement with threaded outer surface 116, e.g., a helical thread pattern, of slide shaft 108. As shown in FIG. 6, thread teeth 504 are pivoted distally and into distal thread teeth pivot apertures 516 of inner slider 502.

In FIG. 6, the inner body (tube) 410 with its supports 410A, 410B are shown connected to the sheath 101 which is shown partially cutaway. Sheath 101 is a hollow tube and includes a pushrod lumen. Pushrod 436 extends through sheath 101. Pushrod 436 is also shown partially cutaway. Pushrod 436 is a hollow tube and includes a lumen. A guide wire lumen 602 extends through pushrod 436. Guide wire lumen 602 is a hollow tube and includes a lumen. Guide wire lumen 602 is also shown partially cutaway. A guide wire 604 extends through guide wire lumen 602. In FIG. 7, pushrod 436, guide wire lumen 602, and guide wire 604 are not illustrated for clarity of presentation.

FIG. 7 is a cross-sectional view of handle assembly 112 of FIG. 6 with hub assembly 104 disengaged from threaded outer surface 116 of slide shaft 108. Referring now to FIGS. 6 and 7 together, thread teeth 504 are curved members. Accordingly, when thread teeth 504 are located in distal thread teeth pivot apertures 516 (FIG. 6), thread teeth 504 pivot on thread teeth pivot supports 520 and protrude above proximal thread teeth pivot apertures 518 of inner slider 502 and into proximal thread teeth pivot apertures 530 of sleeve 432. Conversely, when thread teeth 504 are located in proximal thread teeth pivot apertures 518 (FIG. 7), thread teeth 504 pivot on thread teeth pivot supports 520 and protrude above distal thread teeth pivot apertures 516 of inner slider 502 and into distal thread teeth cutouts 532 of sleeve 432.

Thread teeth 504 are pivoted on thread teeth pivot supports 520 as sleeve 432 is slid longitudinally, e.g., by pulling or releasing thumb slider 114 (see FIG. 4). Specifically, when sleeve 432 is slid proximally by the physician pulling on thumb slider 114, thread teeth press members 534 slide proximally on thread teeth 504. As thread teeth press members 534 slide proximally on thread teeth 504 longitudinally past thread teeth pivot supports 520, thread teeth press members 534 pivot thread teeth 504 and move protruding teeth 552 out of threaded engagement with threaded outer surface 116 of slide shaft 108 such that protruding teeth 552 are spaced apart from threaded outer surface 116 as shown in FIG. 7.

Conversely, when sleeve 432 is slid distally, e.g., by spring 506 upon the physician releasing thumb slider 114, thread teeth press members 534 slide distally on thread teeth 504. As thread teeth press members 534 slide distally on thread teeth 504 longitudinally past thread teeth pivot supports 520, thread teeth press members 534 pivot thread teeth 504 and move protruding teeth 552 into threaded engagement with threaded outer surface 116 of slide shaft 108 as shown in FIG. 6.

Figure 8:
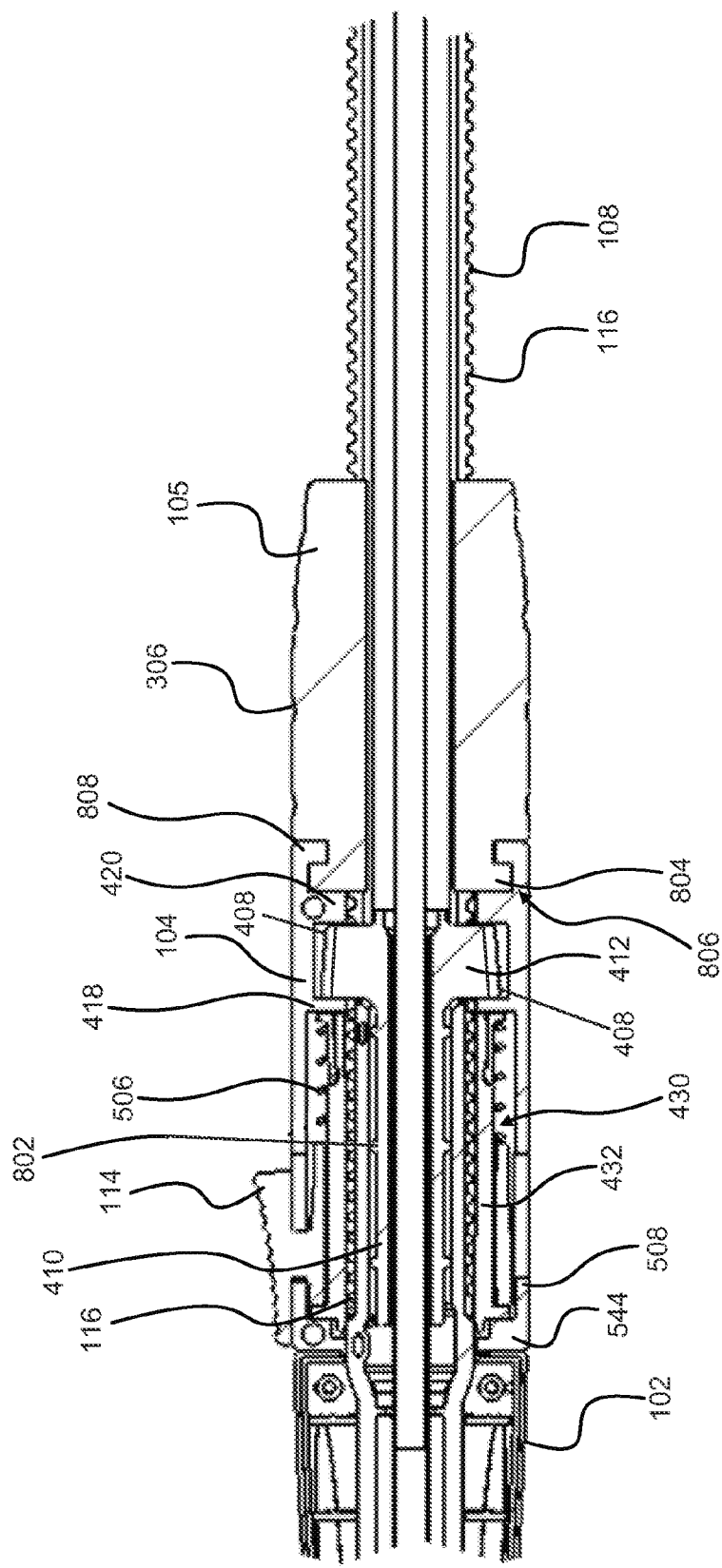
FIG. 8 is a cutaway view of a catheter handle according to one embodiment of the present invention.
Figure 9:
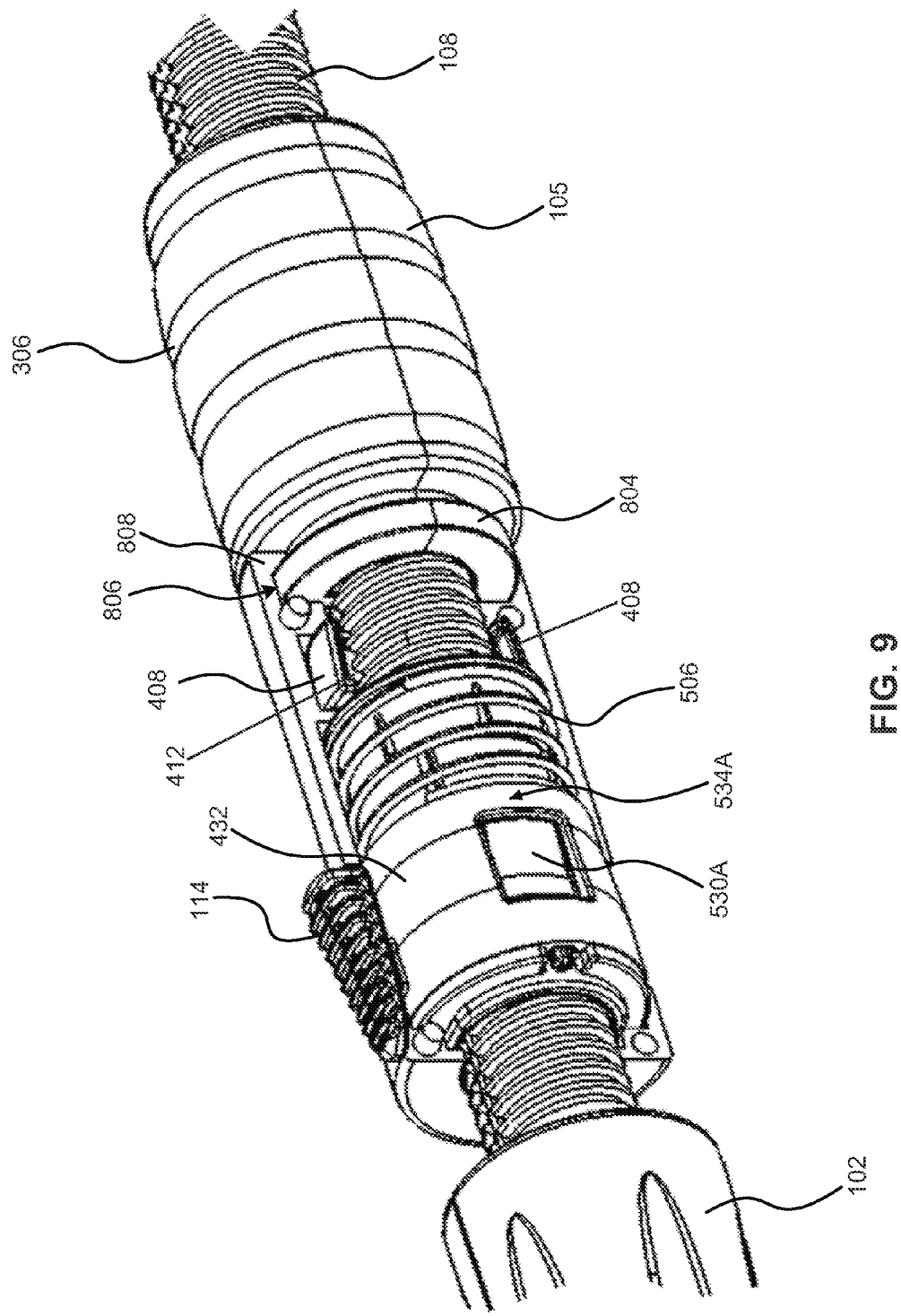
FIG. 9 is a perspective cutaway view of the catheter handle of FIG. 8.

FIGS. 8 and 9 are cutaway views of hub assembly 104 and sliding grip 105 of handle assembly 112. As shown in FIGS. 8 and 9, the proximal end of hub assembly 104 includes a circumferential lip 808 that defines a circumferential notch 806. The distal end of sliding grip 105 includes a circumferential flange 804 that mates with the circumferential notch 806 to connect hub assembly 104 to sliding grip 105. This configuration allows hub assembly 104 to be rotated with respect to sliding grip 105. Hub assembly 104 and sliding grip 105 can be mated together with other suitable configurations that allow hub assembly 104 to be rotated with respect to sliding grip 105.

Figure 10:
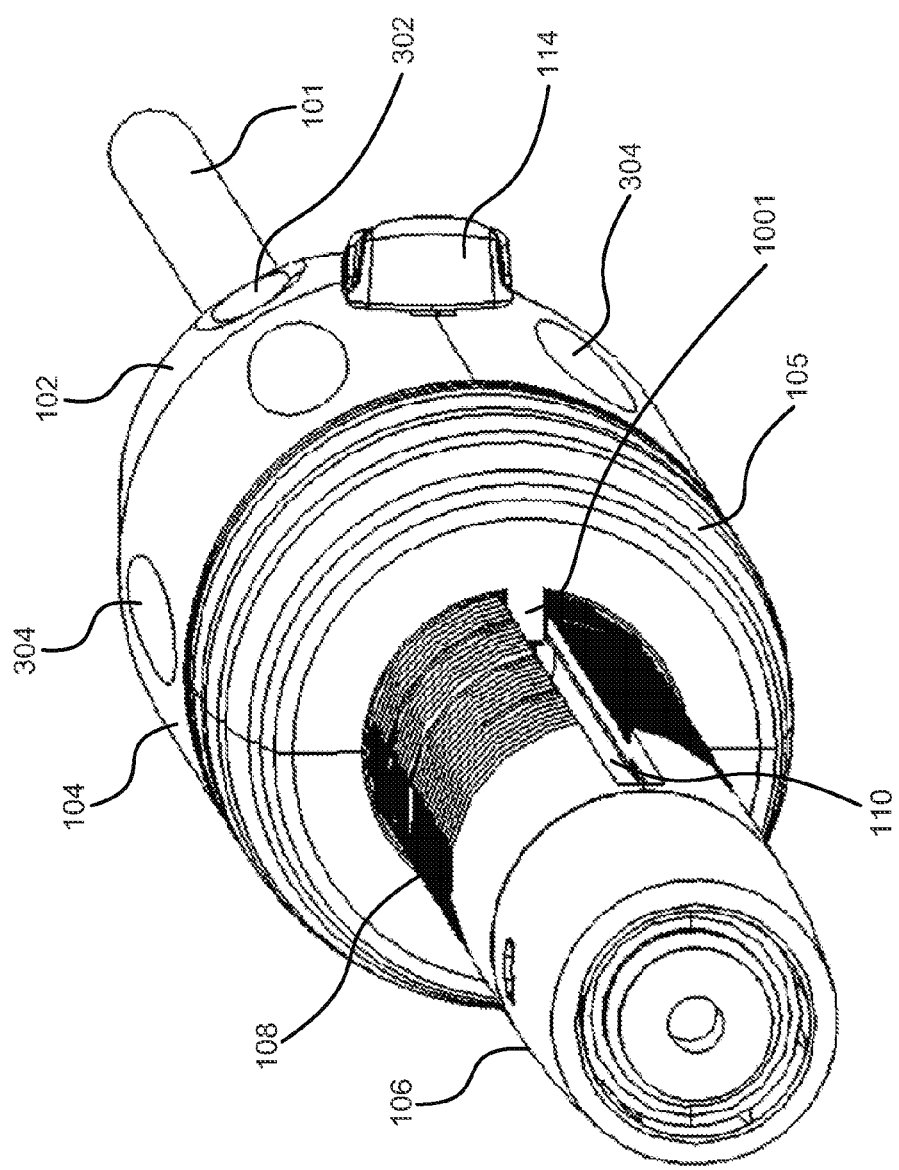
FIG. 10 is a rear perspective view of the catheter handle of FIG. 8.

Referring to FIG. 10, sliding grip 105 includes two inwardly extending tabs 1001 on opposite sides of sliding grip 105. Only one of the inwardly extending tabs 1001 is shown in FIG. 10. Preferably, the second inwardly extending tab is located opposite to the inwardly extending tab 1001 shown in FIG. 10. Tabs 1001 extend into and/or through slots 110 of slide shaft 108 to prevent rotation of sliding grip 105. As a result, sliding grip 105 can move proximally and distally along slide shaft 108, but is prevented from rotating during such movement. Thus, when hub assembly 104 is engaged with the threaded outer surface 116 of slide shaft 108 and a user rotates hub assembly 104, causing hub assembly 104 to move proximally along slide shaft 108, sliding grip 105 will move proximally along shaft 108 but will not rotate. Because sliding grip 105 is rotationally secured to hub assembly 104, sliding grip 105 will also move distally along slide shaft 108 if hub assembly is rotated in an opposite direction, or if thumb slider 114 is operated to allow hub assembly 104 to slide freely along slide shaft 108. This allows a user to brace the palm of the hand on sliding grip 105 while rotating hub assembly 104. Operation of handle assembly 112 can thereby be accomplished with one hand without the need to use a second hand to steady or brace the handle assembly.

The foregoing description of the invention has been presented for purposes of illustration and description. It is not intended to be exhaustive or to limit the invention to the precise form disclosed. Other modifications and variations may be possible in light of the above teachings. The embodiments and examples were chosen and described in order to best explain the principles of the invention and its practical application and to thereby enable others skilled in the art to best utilize the invention in various embodiments and various modifications as are suited to the particular use contemplated. It is intended that the appended claims be construed to include other alternative embodiments of the invention.

EXAMPLES

The following paragraphs serve as examples of the above-described embodiments.

Example 1

One embodiment of the present invention provides a delivery system for delivering a prosthesis 202 to a location in a body. The delivery system includes a slide shaft comprising a threaded outer surface. The slide shaft includes a hollow tubular member with a first longitudinal slot. The slide shaft has a proximal end and a distal end. The delivery system further includes a hub assembly rotatably mounted on the slide shaft, the hub assembly having a slider subassembly for selectively engaging and disengaging the hub assembly with the threaded outer surface. A sliding grip is rotatably coupled to a proximal end of the hub assembly. The sliding grip includes a first tab extending through the first longitudinal slot to prevent rotational movement of the sliding grip relative to the slide shaft. The sliding grip is configured to slide proximally and distally along the slide shaft corresponding to the axial movement of the hub assembly.

The hub assembly can include a circumferential flange defining a circumferential notch on the interior of the proximal end of the hub assembly. The sliding grip can include a circumferential flange configured to engage the circumferential notch to couple the sliding grip to the hub assembly. The slide shaft can include a second longitudinal slot located on an opposite side of the slide shaft from the first longitudinal slot, and the sliding grip can include a second tab extending through the second longitudinal slot. The hub assembly can include a slide having an inner body, an outer body, and couplers extending through the first and second slots to couple the inner body to the outer body. A sheath can also be included with the delivery system. The proximal end of the sheath can be coupled to the hub assembly inside of the slide shaft. The slider subassembly can include a thread tooth comprising a protruding tooth, the thread tooth being pivoted to engage and disengage the hub assembly with the threaded outer surface. The protruding tooth can be threadedly engaged with the threaded outer surface when the hub assembly is engaged with the threaded outer surface. The protruding tooth can be spaced apart from the threaded outer surface when the hub assembly is disengaged from the threaded outer surface. The slider subassembly can also include an inner slider comprising a thread tooth pivot support, the thread tooth being pivotally mounted on the thread tooth pivot support. The thread tooth pivot support can include a protruding pivot pin seated in a pivot aperture of the thread tooth. The inner slider can further include a distal thread tooth pivot aperture and a proximal thread tooth pivot aperture, the thread tooth pivot support being between and separating the distal thread tooth pivot aperture and the proximal thread tooth pivot aperture.

Example 2

Another embodiment provides a method of delivering a prosthesis to a desired location in a body. The method includes introducing a delivery catheter including a catheter handle and a distal tip located distally of the catheter handle into a patient's vasculature. The distal tip of the delivery catheter is then advanced to a desired location in a body. A hub assembly of the catheter handle is then engaged to a threaded outer surface of a slide shaft of the handle, wherein the slide shaft extends between a distal housing of the handle and a proximal housing of the handle, and wherein the hub assembly is coupled to a sheath housing a prosthesis. The hub assembly is rotated to cause axial movement of the hub assembly and corresponding axial movement of a sliding grip coupled to the hub assembly relative to a push rod attached to the catheter handle, wherein axial movement of the hub assembly results in corresponding axial movement of the sheath, and wherein the sliding grip is coupled to the slide shaft such that rotation of the sliding grip relative to the slide shaft is prevented. The hub assembly is then disengaged from the threaded outer surface by pivoting a thread tooth of the hub assembly out of threaded engagement with the threaded outer surface. The hub assembly is then slid on the slide shaft to further retract the sheath.

The slide shaft can include slots, and the sheath can be coupled to a slide of the hub assembly, the slide extending through the slots. The sliding grip can include tabs extending through the slots to prevent rotation of the sliding grip. The hub assembly can include a circumferential flange defining a circumferential notch on the interior of the proximal end of the hub assembly, and the sliding grip can include a circumferential flange configured to engage the circumferential notch to couple the sliding grip to the hub assembly. The prosthesis can be located over the pushrod and the prosthesis is restrained within the sheath. The rotating step can include retracting the sheath to initiate deployment of the prosthesis. The sliding step can include completing the deployment of the prosthesis. The pushrod can include a guide wire lumen. A guide wire can extend through the guide wire lumen.

What is claimed is:

1. A delivery system for delivering a prosthesis to a location in a body, the delivery system comprising:
   a slide shaft comprising a threaded outer surface, wherein the slide shaft comprises a hollow tubular member with a first longitudinal slot, the slide shaft having a proximal end and a distal end;
   a hub assembly rotatably mounted on the slide shaft, the hub assembly comprising a slider subassembly for selectively engaging and disengaging the hub assembly with the threaded outer surface of the slide shaft; and
   a sliding grip rotatably coupled to a proximal end of the hub assembly, wherein the sliding grip includes a first tab extending through the first longitudinal slot to prevent rotational movement of the sliding grip relative to the slide shaft, wherein the sliding grip is configured to slide proximally and distally along the slide shaft corresponding to axial movement of the hub assembly, and wherein the sliding grip is configured to be accessible to a user's hand such that the user's hand directly contacts the sliding grip during deployment of a prosthesis.

2. The delivery system of claim 1, wherein the hub assembly includes a circumferential flange defining a circumferential notch on an interior of the proximal end of the hub assembly, and wherein the sliding grip includes a circumferential flange configured to engage the circumferential notch to couple the sliding grip to the hub assembly.

3. The delivery system of claim 1, wherein the slide shaft includes a second longitudinal slot located on an opposite side of the slide shaft from the first longitudinal slot, and wherein the sliding grip includes a second tab extending through the second longitudinal slot.

4. The delivery system of claim 1 further comprising a sheath, wherein a proximal end of the sheath is coupled to the hub assembly inside of the slide shaft.

5. The delivery system of claim 4, wherein the slider subassembly comprises a thread tooth comprising a protruding tooth, the thread tooth being pivoted to engage and disengage the hub assembly with the threaded outer surface.

6. The delivery system of claim 5, wherein the protruding tooth is threadedly engaged with the threaded outer surface of the slide shaft when the hub assembly is engaged with the threaded outer surface.

7. The delivery system of claim 5, wherein the protruding tooth is spaced apart from the threaded outer surface of the slide shaft when the hub assembly is disengaged from the threaded outer surface.

8. The delivery system of claim 5, wherein the slider subassembly comprises an inner slider comprising a thread tooth pivot support, the thread tooth being pivotally mounted on the thread tooth pivot support.

9. The delivery system of claim 5, wherein the thread tooth pivot support comprises a protruding pivot pin seated in a pivot aperture of the thread tooth.

10. The delivery system of claim 5, wherein the inner slider further comprises a distal thread tooth pivot aperture and a proximal thread tooth pivot aperture, the thread tooth pivot support being between and separating the distal thread tooth pivot aperture and the proximal thread tooth pivot aperture.

11. A delivery system for delivering a prosthesis to a location in a body, the delivery system comprising:
- a slide shaft comprising a threaded outer surface, wherein the slide shaft comprises a hollow tubular member with a first longitudinal slot, the slide shaft having a proximal end and a distal end;
- a hub assembly rotatably mounted on the slide shaft, the hub assembly comprising a slider subassembly for selectively engaging and disengaging the hub assembly with the threaded outer surface of the slide shaft; and
- a sliding grip rotatably coupled to a proximal end of the hub assembly, wherein the sliding grip includes a first tab extending through the first longitudinal slot to prevent rotational movement of the sliding grip relative to the slide shaft, wherein the sliding grip is configured to slide proximally and distally along the slide shaft corresponding to axial movement of the hub assembly, and wherein the sliding grip is configured to be accessible to a user's hand during deployment of a prosthesis,
wherein the hub assembly includes a slide having an inner body within the slide shaft, an outer body outside the slide shaft, and couplers extending through the first longitudinal slot to couple the inner body to the outer body.

12. A delivery system for delivering a prosthesis to a location in a body, the delivery system comprising:
- a slide shaft comprising a threaded outer surface, wherein the slide shaft comprises a hollow tubular member with a first longitudinal slot, the slide shaft having a proximal end and a distal end;
- a hub assembly rotatably mounted on the slide shaft, the hub assembly comprising a slider subassembly for selectively engaging and disengaging the hub assembly with the threaded outer surface of the slide shaft; and
- a sliding grip rotatably coupled to a proximal end of the hub assembly, wherein the sliding grip includes a first tab extending through the first longitudinal slot to prevent rotational movement of the sliding grip relative to the slide shaft, wherein the sliding grip is configured to slide proximally and distally along the slide shaft corresponding to axial movement of the hub assembly, and wherein the sliding grip is configured to be accessible to a user's hand during deployment of a prosthesis,
wherein the hub assembly and the sliding grip are configured such that a user can brace a palm of the user on the sliding grip while the user rotates the hub assembly with fingers of the user.

\* \* \* \* \*